United States Patent [19]

Kameswaran

[11] Patent Number: 5,631,379
[45] Date of Patent: May 20, 1997

[54] OXAZOLE AMINES AS INTERMEDIATES IN THE MANUFACTURE OF INSECTICIDAL PYRROLES

[75] Inventor: Venkataraman Kameswaran, Princeton Junction, N.J.

[73] Assignee: American Cyanamid Company, Madison, N.J.

[21] Appl. No.: 343,154

[22] Filed: Nov. 22, 1994

[51] Int. Cl.$^6$ ............................................. C07D 263/28
[52] U.S. Cl. ...................................................... 548/233
[58] Field of Search .................................. 548/233

[56] References Cited

U.S. PATENT DOCUMENTS

| | | | |
|---|---|---|---|
| 3,290,326 | 12/1966 | Hoffer | 548/233 |
| 3,457,294 | 7/1969 | Crovetti et al. | |
| 4,150,143 | 4/1979 | Neville et al. | 548/233 |
| 5,030,735 | 7/1991 | Addor et al. | 548/531 |
| 5,145,986 | 9/1992 | Kameswaran et al. | 548/531 |
| 5,288,901 | 2/1994 | Doehner, Jr. et al. | 562/449 |
| 5,426,225 | 6/1995 | Kameswaran | 564/212 |
| 5,480,902 | 1/1996 | Addor et al. | 548/228 |

FOREIGN PATENT DOCUMENTS

| | | |
|---|---|---|
| 0530147 | 8/1992 | European Pat. Off. |
| 0102875 | 6/1982 | Japan ............ 548/233 |
| 92-05163 | 4/1992 | WIPO ............ 548/233 |

OTHER PUBLICATIONS

*J. Chem. Soc.*, Chemical Communications, 2, 1993, 101–102.
*Chemical Abstracts*, 122 (9), 1995, 105575 (Abstract), 1018.
*Chemical Abstracts*, 120 (19) 1994, 244658 (Abstract), 891.
*Chemical Abstracts*, 115 (11) 1991, 114396 (Abstract), 1001.
Deyrup, J.A. and Killion, K.K., *Journal of Heterocyclic Chemistry*, 9 (5) 1045–48 (1972).
Poupert, J., et al., *Synthesis* (11), 622–4 (1972).
Tanaka, C., and Haruko, A., *Yakugaku Zasshi*, 91 (4), 436–43 (Abstract) (1971).
McEwen, W.E., et al., *Journal of Organic Chemistry*, 1980, 45, 1301–1308.
Jones, R.A., *Pyrroles, Part One*, J. Wiley and Sons, (1990) 167–170.

*Primary Examiner*—Donald G. Daus
*Attorney, Agent, or Firm*—John W. Hogan, Jr.

[57] ABSTRACT

The present invention provides 5-amino-4-aryl-2-perfluoroalkyl-1,3-oxazole derivatives, a method for the preparation of said derivatives and their use as a key intermediate in the manufacture of insecticidal, acaricidal and nematocidal arylpyrrole compounds.

20 Claims, No Drawings

OXAZOLE AMINES AS INTERMEDIATES IN THE MANUFACTURE OF INSECTICIDAL PYRROLES

BACKGROUND OF THE INVENTION

Arylpyrrole carbonitrile compounds are highly effective insecticidal, acaricidal and nematocidal agents with a unique mode of action and a broad spectrum of activity. In particular, 2-aryl-5-(trifluoromethyl)pyrrole-3-carbonitrile compounds demonstrate effective control across a wide array of pests and can control resistant pests such as pyrethroid-, organophosphate-, cyclodiene-, organochlorine-, organotin-, carbamate-, and benzophenylurea-resistant biotypes of Helicoverpa/Heliothis spp., Spodoptera spp., Trichoplusia spp., Pseudoplusia spp. and Tetranychus spp. Because there is no apparent cross-resistance, 2-aryl-5-trifluoromethylpyrrole-3-carbonitrile compounds and their derivatives have potential for use in resistance management programs. Further, said pyrroles have little effect on beneficial species making them excellent candidates for integrated pest management programs, as well. These programs are essential in today's crop production.

Therefore, methods to prepare said pyrroles and intermediates to facilitate their manufacture are of great value. Among the present methods to prepare 2-aryl-5-trifluoromethylpyrrole-3-carbonitrile compound on a manufacturing scale is the 1,3-dipolar cycloaddition of 3-oxazolin-5-one with 2-chloroacrylonitrile (U.S. Pat. No. 5,030,735).

It is an object of this invention to provide 5-amino-4-aryl-2-perfluoroalkyl-1,3-oxazole derivatives useful as key intermediates in the manufacture of insecticidal, acaricidal and nematocidal pyrrole compounds.

It is another object of this invention to provide a facile method of preparation of said oxazole intermediates.

It is a further object of this invention to provide an alternate source of important intermediate compounds and manufacturing routes for the production of a new class of highly effective pesticidal compounds.

SUMMARY OF THE INVENTION

The present invention provides 5-amino-4-aryl-2-perfluoroalkyl-1,3-oxazole derivative of formula I

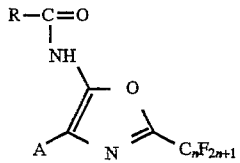
(I)

wherein n is an integer of 1, 2, 3, 4, 5, 6, 7 or 8;

R is $C_1$–$C_6$alkyl, $C_1$–$C_6$haloalkyl, $COOR_1$, or phenyl optionally substituted with one or more halogen, $NO_2$, CN, $C_1$–$C_4$alkoxy, $C_1$–$C_4$alkylthio, $C_1$–$C_4$alkyl or $C_1$–$C_4$haloalkyl groups;

A is

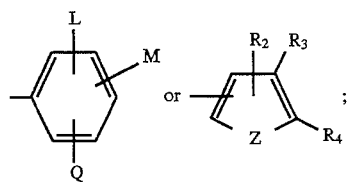

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure
—$OCH_2O$—, —$OCF_2O$— or —CH=CH—CH=CH—;

$R_1$ is $C_1$–$C_4$alkyl or $C_1$–$C_4$haloalkyl;

$R_2$, $R_3$ and $R_4$ are each independently hydrogen, halogen, $NO_2$, CHO or $R_3$ and $R_4$ may be taken together with the atoms to which they are attached to form a ring in which $R_3R_4$ is represented by the structure

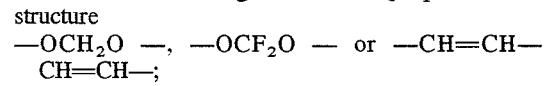

$R_5$, $R_6$, $R_7$ and $R_8$ are each independently hydrogen, halogen, CN or $NO_2$; and Z is O or S; or

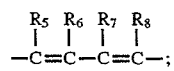 the tautomers thereof.

The present invention further provides a method for the preparation of the oxazole amine formula I compounds and methods for their use as a key intermediate in pesticidal arylpyrrole manufacture.

DETAILED DESCRIPTION OF THE INVENTION

Processes useful on a manufacturing scale preferentially contain key intermediate compounds which may be obtained in high to quantitative yield. These key intermediates are stable either upon isolation or in situ, may be produced from simple or readily available starting materials and may be readily converted to the desired end product. Ideally the process contains a minimum of reaction steps, results in optimum yield and purity, and if applicable, generates regio-or stereospecific products.

It has now been found that 5-amino-4-aryl-2-perfluoroalkyl-1,3-oxazole derivatives of formula I are effective key intermediates in the manufacture of 2-aryl-5-trifluoromethylpyrrole-3-carbonitrile insecticidal, acaricidal and nematicidal compounds. The oxazole amine derivatives of the present invention have the structure of formula I

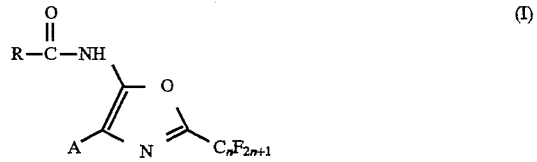
(I)

wherein n is an integer of 1, 2, 3, 4, 5, 6, 7 or 8;

R is $C_1$-$C_6$alkyl, $C_1$-$C_6$haloalkyl, $COOR_1$, or phenyl optionally substituted with one or more halogen, $NO_2$, CN, $C_1$-$C_4$alkoxy, $C_1$-$C_4$alkylthio, $C_1$-$C_4$alkyl or $C_1$-$C_4$haloalkyl groups;

A is

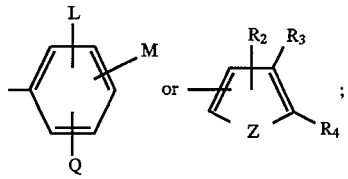

L is hydrogen or halogen;

M and Q are each independently hydrogen, halogen CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl or when M and Q are on adjacent positions they may be taken together with the carbon atoms to which they are attached to form a ring in which MQ represents the structure
—$OCH_2O$—, —$OCF_2O$— or —CH=CH—CH=CH—;

$R_1$ is $C_1$-$C_4$alkyl or $C_1$-$C_4$haloalkyl;

$R_2$, $R_3$ and $R_4$ are each independently hydrogen, halogen, $NO_2$, CHO or $R_3$ and $R_4$ may be taken together with the atoms to which they are attached to form a ring in which $R_3R_4$ is represented by the structure

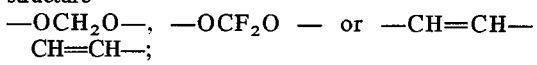

$R_5$, $R_6$, $R_7$ and $R_8$ are each independently hydrogen, halogen, CN or $NO_2$; and Z is O or S.

The compounds of formula I may also be represented as their tautomeric 5-imino-4-aryl-2-(perfluoroalkyl)oxazoline structures, Ia and Ib, as shown below.

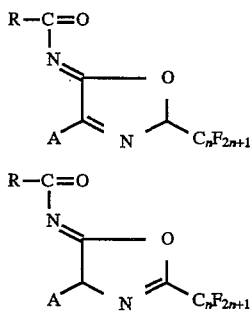

The term halogen designates Cl, Br, F, or I and the term haloalkyl encompasses an alkyl group with n carbons which contains from one to 2n+1 halogen atoms.

Intermediates of formula I are readily prepared by cyclizing perfluoroalkanoyl aminonitrile compounds of formula II

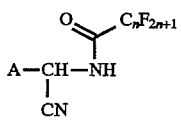

wherein A is as defined hereinabove in the presence of an acid and an acyl halide of formula III.

wherein X is Cl or Br and R is as defined hereinabove, optionally in the presence of a solvent. The reaction is shown in flow diagram I.

Flow Diagram I

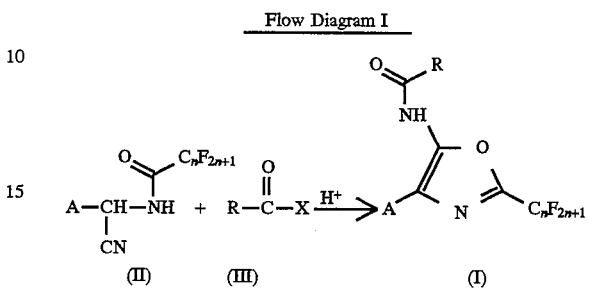

Compounds of formula II and their preparation are described in co-pending patent application Ser. No. 08/175,845 filed Dec. 30, 1993 (now U.S. Pat. No. 5,426,225) and incorporated herein by reference thereto.

Among the solvents suitable for use in the preparation of the formula I intermediate are aromatic hydrocarbons and halogenated aromatic hydrocarbons, preferably aromatic hydrocarbons such as toluene, benzene, xylene, and the like, more preferably toluene or xylene or mixtures thereof.

Acids suitable for use in the cyclization include sulfuric acid, methanesulfonic acid, benzenesulfonic acid, p-toluenesulfonic acid, fluoroboric acid, boron trifluoride complexes and the like. Boron trifluoride complexes may include $BF_3$ etherate, $BF_3$methanol complex, $BF_3$ ethanol complex and the like.

Surprisingly, it has been found that the formula I oxazole amine intermediate undergoes a 1,3-dipolar cycloaddition with 2-haloacrylonitrile or 2,3-dihalopropionitrile in the presence of a base and optionally in the presence of a solvent to regiospecifically give 2-aryl-5-perfluoroalkylpyrrole-3-carbonitrile compounds of formula IV in a simple one step conversion. The reaction, using 2-haloacrylonitrile as the 1,3-dipolarifile, is shown in flow diagram II wherein X is Cl or Br.

Flow Diagram II

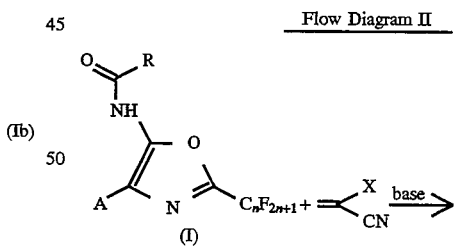

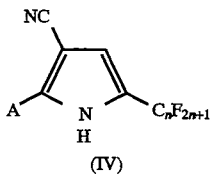

Among the bases which may be used in the inventive process are alkali metal carbonates or bicarbonates, tri($C_1$-$C_4$alkyl)amines, alkali metal hydroxides, alkali metal acetates, 4-dimethylaminopyridine, pyridine, and the like. Preferred bases are alkali metal carbonates and tri($C_1$-$C_4$alkyl)amines such as triethylamine.

Solvents contemplated for use in the preparation of formula IV compounds are those organic solvents which are commonly suitable for manufacturing processes and in which the reactants are soluble such as acetonitrile, toluene, xylene, dimethyl formamide and the like or combinations thereof.

In accordance with the process of the invention a perfluoroalkanoyl aminonitrile of formula II is admixed with approximately an equimolar amount of an acylhalide of formula III in the presence of an acid, optionally in the presence of a solvent to form the formula I oxazole amine intermediate. Said intermediate may be isolated using conventional techniques such as filtration or extraction. The rate of formation of the formula I oxazole may be increased with increased temperature. However, it is understood that excessively high reaction temperatures will cause decomposition and a decrease in product yield and purity. Typical reaction temperatures may range from 20°–100° C., preferably 60°–90° C. The isolated oxazole amine intermediate may then be converted to the desired formula IV arylpyrrole product by admixing said oxazole with about one molar equivalent of 2-haloacrylonitrile or 2,3-dihalopropionitrile in the presence of at least one molar equivalent of a base and optionally in the presence of a solvent.

In one embodiment of the inventive process the formula I oxazole amine intermediate may be formed in situ and, without isolation, converted directly to the desired regiospecific arylpyrrole product from the formula II perfluoroalkanoyl aminonitrile starting material as shown in flow diagram III.

Flow Diagram III

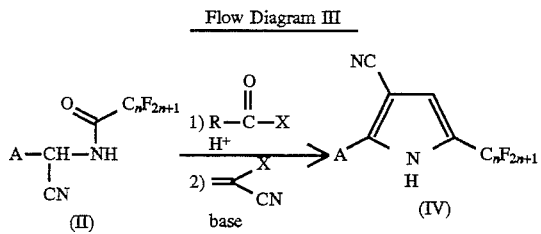

In this embodiment of the invention, the perfluoroalkanoyl aminonitrile of formula II is admixed with about one molar equivalent of an acylhalide of formula III in the presence of an acid and optionally in the presence of a solvent. When the formation of the formula I oxazole amine is complete, the reaction mixture is treated with at least one molar equivalent of 2-haloacrylonitrile, or 2,3-dihalopropionitrile, and at least one molar equivalent of a base. The formula IV arylpyrrole product may be isolated by conventional methods such as dilution of the reaction mixture with water followed by filtration or extraction.

In order to provide a more clear understanding of the invention, the following examples are set forth below. These examples are merely illustrative and are not to be understood to limit the scope or underlying principles of the invention in any way. The terms $^1$HNMR, $^{13}$CNMR and $^{19}$FNMR designate proton, carbon 13 and fluorine 19 nuclear magnetic resonance, respectively. The term HPLC designates high performance liquid chromatography and GLC designates gas-liquid chromatography.

EXAMPLE 1

Preparation of N-4-(p-Chlorophenyl)-2-(trifluoromethyl)-5-oxazolylacetamide

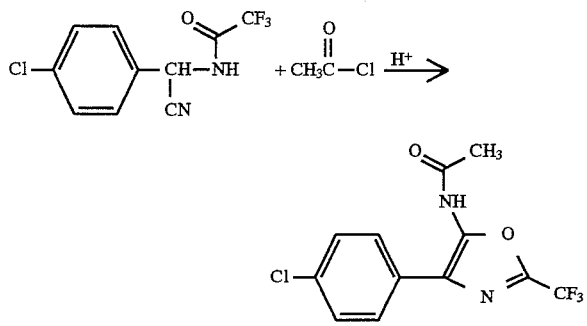

A slurry of N-[(p-chlorophenyl cyanomethyl]-2,2,2-trifluoroacetamide (13.1, 0.05 mol in toluene is treated with methanesulfonic acid (2.4 g, 0.025 mol) at room temperature. The reaction mixture is treated with acetyl chloride (4.32 g, 0.055 mol), heated at 80° C. for 2 hours, cooled and filtered. The filter cake is dissolved in ethyl acetate, washed with water and concentrated in vacuo to give a residue. The residue is crystallized from ethyl acetate/heptane to give the title product as a white solid, 13.8 g (90% yield) mp 207.5°–208.5° C., identified by IR, $^1$HNMR, $^{13}$CNMR and $^{19}$FNMR analyses.

EXAMPLE 2

Preparation of Ethyl N-4-(p-Chlorophenyl)-2-(trifluoromethyl)-5-oxazolyloxamate

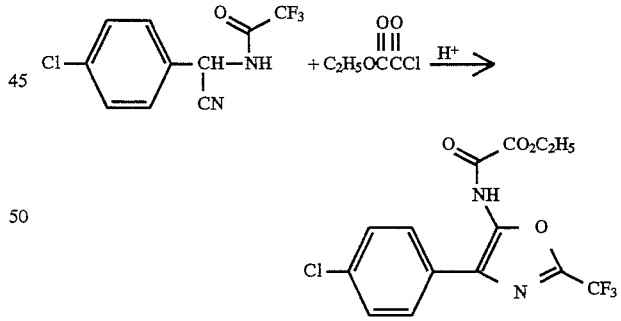

A stirred mixture of N-[(p-chlorophenyl)cyanomethyl]-2,2,2-trifluoroacetamide (39.4 g, 0.15 mol), methanesulfonic acid (14.4 g, 0.015 mol) and ethyl oxalyl chloride (22.5 g, 0.165 mol) in toluene is heated at 80° C. for 2 hours, cooled to room temperature and diluted with ethyl acetate. The reaction solution is washed with water and concentrated in vacuo to give a solid residue. The residue is recrystallized from toluene-heptane to give the title product as white crystals, 41.8 g (70% yield), mp 107.0°–108.5° C., identified by IR, $^1$HNMR, $^{13}$CNMR and $^{19}$FNMR analyses.

EXAMPLE 3

Preparation of 5-(Acylamino)-4-aryl-2-perfluoroalkyl-1,3-oxazole

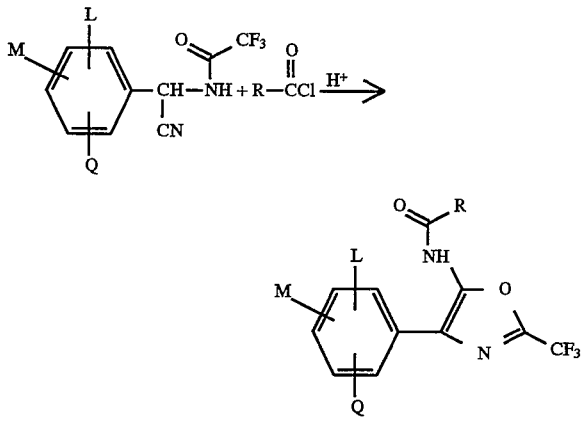

Using essentially the same procedures described in Examples 1 and 2 hereinabove the following acyamino oxazoles shown in Table I are obtained.

TABLE I

| L | M | Q | R | mp °C. |
|---|---|---|---|---|
| H | 4-CF₃ | H | —CH₃ | 187.0–187.5 |
| H | 4-Br | H | —CH₃ | 215.0–216.0 |
| 3-Cl | 4-Cl | H | —CH₃ | 171.0–172.0 |
| H | 4-Cl | H | —C₆H₅ | 172–176 |
| H | 4-CF₃ | H | —C₆H₅ | 146–149 |
| H | 4-Br | H | —C₆H₅ | 167–170 |
| 3-Cl | 4-Cl | H | —C₆H₅ | 180–182 |
| H | —OCF₂O— | | —C₂H₅ | — |

EXAMPLE 4

Preparation of 2-(p-Chlorophenyl)-5-(trifluoromethyl)pyrrole-3-carbonitrile

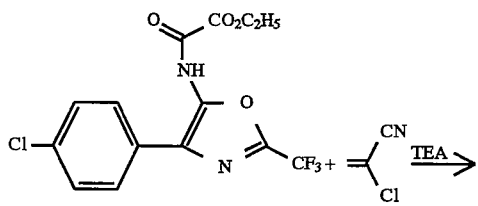

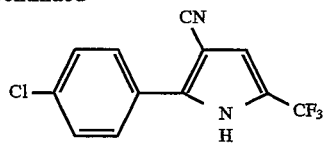

A solution of ethyl N-4-(p-chlorophenyl)-2-(trifluoromethyl)-5-oxazolyloxamate (10.9 g, 0.03 mol) in acetonitrile is treated with 2-chloroacrylonitrile at room temperature. The reaction mixture is treated dropwise with triethylamine (TEA)(7.3 g, 0.072 mol), heated at 70°–72° C. for 5 hours, cooled to room temperature and diluted with water. The diluted reaction mixture is extracted with ethyl acetate. The extracts are combined, washed with water and concentrated in vacuo to give a semisolid residue. The residue is dissolved in 1:1 ethyl acetate:heptane and filtered through silica gel. The filtrate is concentrated in vacuo to give a solid residue. The solid is recrystallized from ethyl acetate-heptane to give the title product as a white solid, 4.6 g (57% yield), mp 238°–241° C., identified by ¹HNMR, ¹⁹FNMR, GLC and HPLC analyses.

EXAMPLE 5

Preparation of 2-(p-Chlorophenyl)-5-(trifluoromethyl)pyrrole-3-carbonitrile

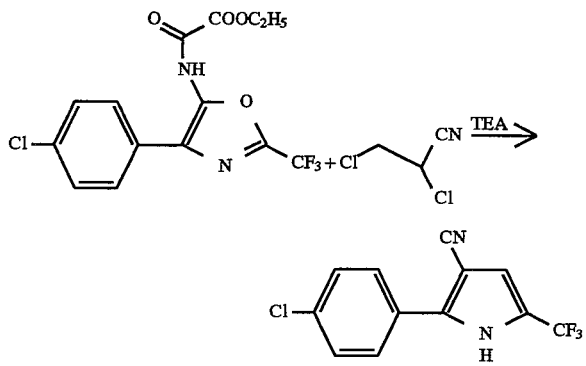

Using essentially the same procedure described above in Example 4 and substituting 2,3-dichloropropionitrile in place of 2-chloroacrylonitrile and employing 3.4 equivalents of triethylamine, the title product is obtained in 58% yield.

EXAMPLE 6

Preparation of 2-(p-Chlorophenyl)-5-(trifluoromethyl)pyrrole-3-carbonitrile

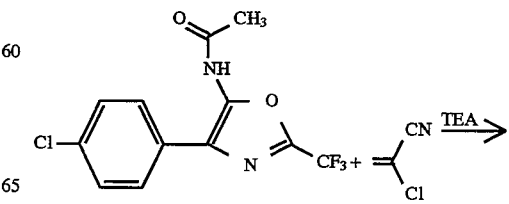

-continued

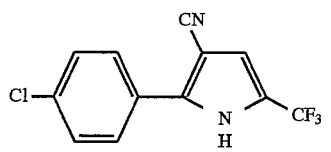

A slurry of N-4-(p-chlorophenyl)-2-(trifluoromethyl)-5-oxazolylacetamide (9.2 g, 0.03 mol) in acetonitrile is treated with 2-chloroacrylonitrile (3.15 g, 0.036 mol). The reaction mixture is treated dropwise with triethylamine (7.3 g, 0.072 mol), heated at 72°–75° C. for 2 hours, cooled to room temperature and diluted with water. The diluted mixture is extracted with ethyl acetate. The extracts are combined, washed with water and concentrated in vacuo to give a semi-solid residue. Flash chromatography of the residue (silica gel, 15% ethyl acetate in heptane eluent) gives the title product as a pale yellow solid, 3.7 g (46% yield), mp 238°–241° C., identified by $^1$HNMR and $^{19}$FNMR analyses.

EXAMPLE 7

Preparation of 2-(p-Chlorophenyl)-5-(trifluoromethyl)pyrrole-3-carbonitrile

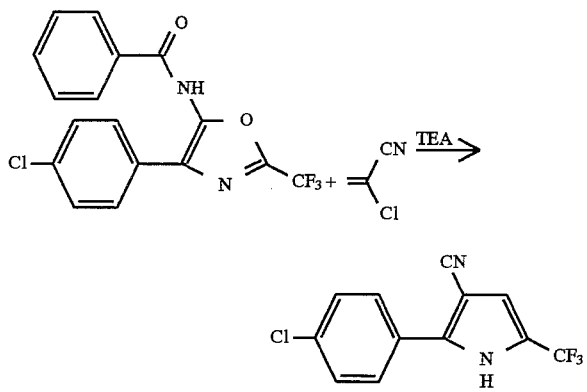

A slurry of N-4(p-chlorophenyl)-2-(trifluoromethyl)-5-oxazolylbenzamide (14.7 g, 0.04 mol) in acetonitrile is treated with 2-chloroacrylonitrile (4.2 g, 0.048 mol). The reaction mixture is treated dropwise with triethylamine (9.72 g, 0.096 mol), heated at 70°–72° C. for 1 hour, cooled to room temperature and diluted with water. The diluted mixture is extracted with ethyl acetate. The extracts are combined, washed with water and concentrated in vacuo to give a waxy solid residue. Flash chromatography (silica-gel; 15% ethyl acetate in heptane as eluent) gives the title product as a pale yellow solid, 6.2 g (47% yield), mp 240°–242° C., identified by $^1$HNMR and $^{19}$FNMR analyses.

EXAMPLE 8

Preparation of 2-Aryl-5-perfluoroalkylpyrrole-3-carbonitrile

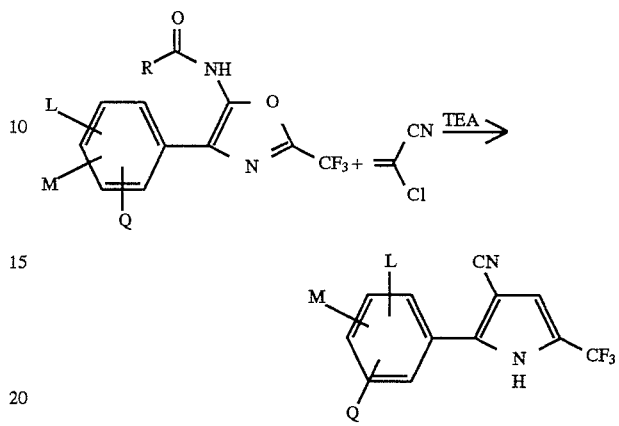

Using essentially the same procedures described in Examples 4-7 and employing the appropriate oxazole amine starting material, the following pyrrole compounds in Table II are obtained.

TABLE II

| Oxazole R | L | M | Q | mp °C. | % Yield |
|---|---|---|---|---|---|
| —CH$_3$ | H | 4-Br | H | >230 | 69 |
| —CH$_3$ | H | 4-CF$_3$ | H | 219–220 | 58 |
| —CH$_3$ | 3-Cl | 4-Cl | H | >240 | 64 |
| —C$_6$H$_5$ | H | 4-Br | H | >230 | 28 |

EXAMPLE 9

Preparation of 2-(p-Chlorophenyl)-5-(trifluoromethyl)pyrrole-3-carbonitrile

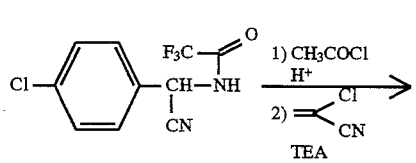

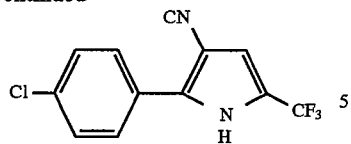

A slurry of N-[(p-chlorophenyl)cyanomethyl]-2,2,2-trifluoroacetamide (13.1 g, 0.05 mol) in toluene is treated sequentially with methanesulfonic acid (2.4 g, 0.025 mol) and acetyl chloride (4.32 g, 0.055 mol), at room temperature, heated at 80° C. for 2 hours, cooled to room temperature, diluted with acetonitrile, treated first with 2-chloroacrylonitrile (5.25 g, 0.06 mol) then dropwise with triethylamine (13.7 g, 0.135 mol), heated at 70°–72° C. for 1 hour, cooled to room temperature and diluted with water. The mixture is extracted with ethyl acetate. The extracts are combined, washed with water and concentrated in vacuo to give a residue. Flash chromatography (silica-gel; 15% ethyl acetate in heptane as eluent) to give the title product.

I claim:

1. A compound having the structure of formula I

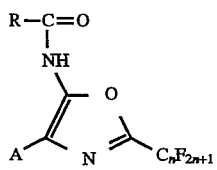

wherein n is an integer of 1, 2, 3, 4, 5, 6, 7 or 8;

R is $C_1$–$C_6$alkyl, $C_1$–$C_6$haloalkyl, $COOR_1$, or phenyl;

A is

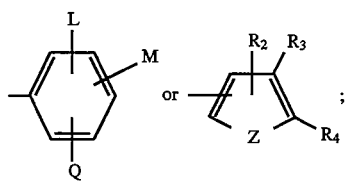

L is hydrogen or halogen;

M and Q are each independently hydrogen, halogen CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —$OCH_2O$ —, —$OCF_2O$ — or —CH=CH—CH=CH—;

$R_1$ is $C_1$–$C_4$alkyl or $C_1$–$C_4$haloalkyl;

$R_2$, $R_3$ and $R_4$ are each independently hydrogen or halogen and

Z is O or S; or the tautomers thereof.

2. The compound according to claim 1 wherein R is $C_1$–$C_6$alkyl, $COOR_1$, or phenyl.

3. The compound according to claim 1 wherein n is an integer of 1 or 2.

4. The compound according to claim 3 wherein A is

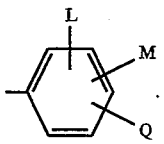

5. The compound according to claim 4 wherein L is hydrogen and M and Q are each independently hydrogen, halogen or $C_1$–$C_4$haloalkyl.

6. The compound according to claim 4 wherein R is $C_1$–$C_6$alkyl, $COOR_1$ or phenyl.

7. The compound according to claim 6 wherein $R_1$ is $C_1$–$C_4$alkyl; L is hydrogen and M and Q are each independently hydrogen, halogen or $C_1$–$C_4$haloalkyl.

8. The compound according to claim 7 N-4-(p-chlorophenyl)-2-(trifluoromethyl)-5-oxazolylacetamide.

9. The compound according to claim 7 N-4-(p-chlorophenyl)-2-(trifluoromethyl)-5-oxazolylbenzamide.

10. The compound according to claim 7 ethyl N-4-(p-chlorophenyl)-2-(trifluoromethyl)-5-oxazolyloxamate.

11. The compound according to claim 7 N-4-($\alpha,\alpha,\alpha$-trifluoro-p-tolyl)-2-(trifluoromethyl)-5-oxazolylacetamide.

12. The compound according to claim 7 N-4-(3,4-dichlorophenyl)-2-(trifluoromethyl)-5-oxazolylacetamide.

13. The compound according to claim 7 N-4-(3,5-dichlorophenyl)-2-(trifluoromethyl)-5-oxazolylacetamide.

14. The compound according to claim 2 wherein A is

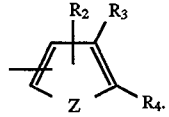

15. The compound according to claim 14 wherein $R_2$ is in the 3 position and is hydrogen.

16. The compound according to claim 15 wherein $R_3$ and $R_4$ are each independently hydrogen or halogen and Z is S.

17. The compound according to claim 16 N-4-(2-thienyl)-2-(trifluoromethyl)-5-oxazolylacetamide.

18. A method for the preparation of a compound of formula I

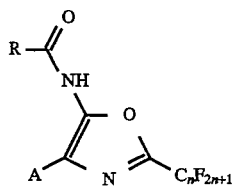

wherein n, R and A are described in claim 1 which comprises reacting a compound of formula II

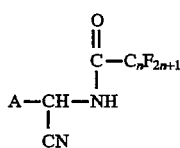

with at least one molar equivalent of a compound of formula III

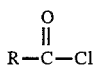 (III)

and an acid selected from the group consisting of sulfuric acid, methanesulfonic acid, benzenesulfonic acid, p-toluenesulfonic acid, fluoroboric acid, and boron trifluoride complexes, optionally in the presence of a solvent.

19. The method according to claim 18 wherein the acid is methanesulfonic acid, p-toluenesulfonic acid, sulfuric acid, benzenesulfonic acid, naphthalenesulfonic acid, fluoroboric acid or a boron trifluoride complex.

20. The method according to claim 19 wherein the solvent is toluene, xylene or a combination thereof.

* * * * *